United States Patent [19]

Marrelli et al.

[11] Patent Number: 5,001,434
[45] Date of Patent: Mar. 19, 1991

[54] VARIABLE MODE MICROWAVE WATER CUT MONITOR AND METHOD

[75] Inventors: John D. Marrelli; David J. Stavish, both of Houston, Tex.

[73] Assignee: Texaco Inc., White Plains, N.Y.

[21] Appl. No.: 337,016

[22] Filed: Apr. 10, 1989

[51] Int. Cl.⁵ .......................................... G01R 27/04
[52] U.S. Cl. .................... 324/640; 324/698; 374/122; 374/142
[58] Field of Search ................. 374/122; 324/58.5 A, 324/640, 698

[56] References Cited

U.S. PATENT DOCUMENTS

| | | | |
|---|---|---|---|
| 3,498,112 | 3/1970 | Howard | 324/58.5 A |
| 3,501,692 | 3/1970 | Kluck | 324/58.5 A |
| 4,240,028 | 12/1980 | Davis, Jr. | 324/665 |
| 4,485,284 | 11/1984 | Pakulis | 374/142 X |
| 4,651,085 | 3/1987 | Sakurai et al. | 324/58.5 A X |
| 4,767,982 | 8/1988 | Florig et al. | 324/58.5 A |
| 4,774,680 | 9/1986 | Agar | 73/61.1 R |
| 4,820,970 | 4/1989 | Swanson | 324/58.5 A |
| 4,881,412 | 11/1989 | Northedge | 73/861.04 |

*Primary Examiner*—Daniel M. Yasich
*Attorney, Agent, or Firm*—Robert A. Kulason; James J. O'Loughlin; Ronald G. Gillespie

[57] ABSTRACT

A variable mode microwave water cut monitor includes a test cell which contains a fluid sample. Apparatus controls the provision and removal of the fluid sample to effect different modes of operation for the monitor, a normal test mode and at least two calibration modes. A source provides microwave energy to one of a first antenna which in turn provides the fluid sample in the test cell with microwave energy. A second antenna receives the microwave energy that has passed through the fluid sample. A detector detects the received microwave energy and provides a signal corresponding thereto. An indicator provides an indication of the water cut of the fluid sample in accordance with the received signal power, a phase difference between the source provided microwave energy and the received microwave energy and internally recorded calibration data for water alone and oil alone.

9 Claims, 2 Drawing Sheets

VARIABLE MODE MICROWAVE WATER CUT MONITOR AND METHOD

BACKGROUND OF THE INVENTION

Field of the Invention

The present invention relates to water cut monitors in general and, more particularly, to microwave water cut monitors.

SUMMARY OF THE INVENTION

A variable mode microwave water cut monitor includes a test cell which contains a fluid sample. Apparatus controls the providing and removal of the fluid sample to effect different modes of operation for the monitor. A source provides microwave energy to one of a first antenna which in turn provides the fluid sample in the test cell with microwave energy. A second antenna receives the microwave energy that has passed through the fluid sample. A detector detects the received microwave energy and provides a signal corresponding thereto. An indicator provides an indication of the water cut of the fluid sample in accordance with the received signal power and a phase difference between the source provided microwave energy and the received microwave energy.

The objects and advantages of the invention will appear more fully hereinafter from a consideration of the detailed description which follows, taken together with the accompanying drawing wherein one embodiment of the invention is illustrated by way of example. It is to be expressly understood, however, that the drawings are for illustration purposes only and are not to be construed as defining the limits of the invention.

DESCRIPTION OF THE INVENTION

Figure 1:
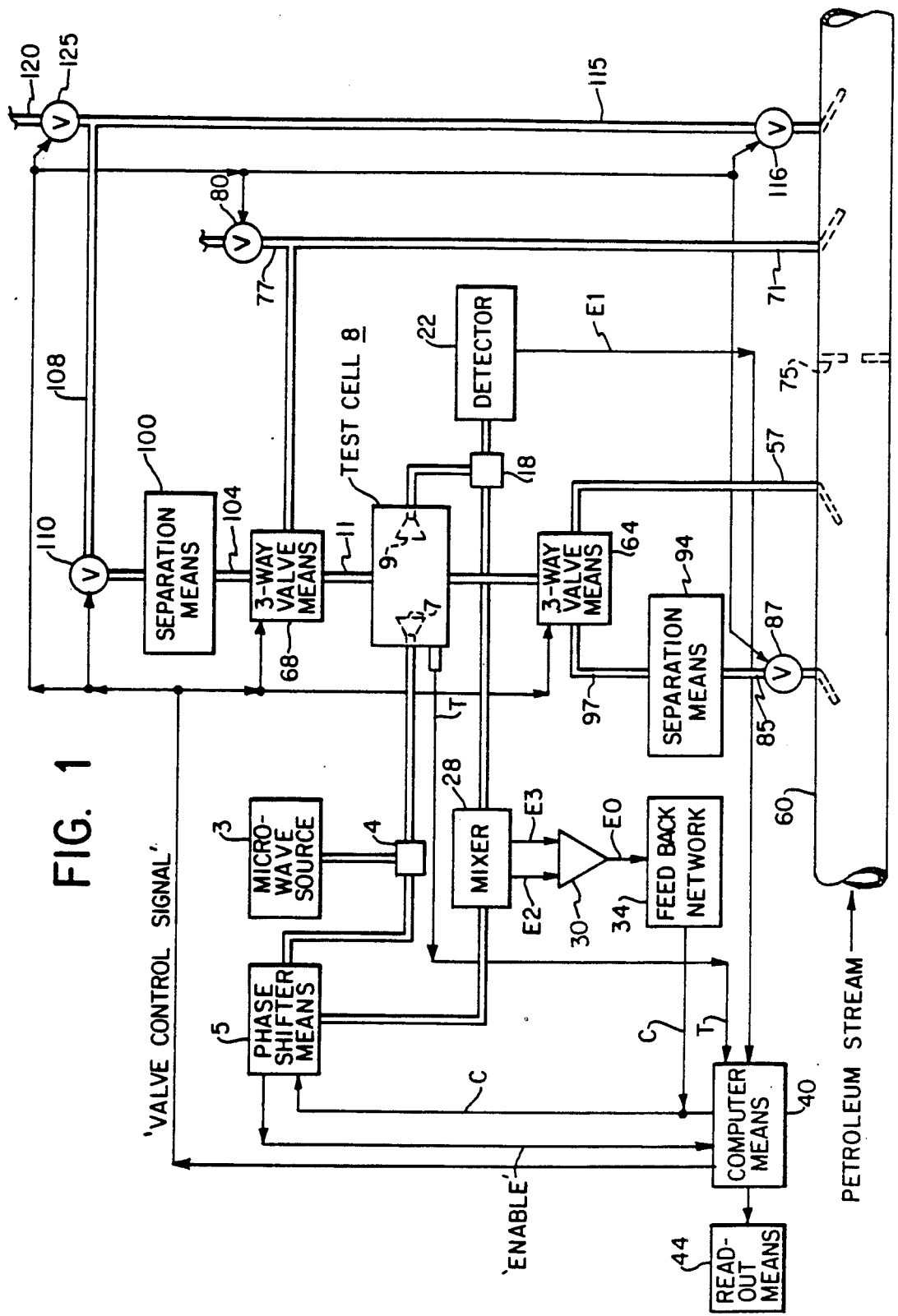
FIG. 1 is a partial simplified block diagram and a partial schematic of a variable mode microwave water cut monitor constructed in accordance with the present invention.

The water cut monitor shown in FIG. 1 includes a microwave source 3 providing electromagnetic energy, hereinafter referred to as microwave energy, at a microwave frequency. Source 3 is low powered and may use a microwave gun source. Source 3 provides microwave energy to directional coupler 4. Directional coupler 4 provides microwave energy to a conventional type voltage controlled phase shifter means 5 and to an antenna 7 in a test cell 8. All conductance or carrying of microwave energy is accomplished by using conventional type waveguides and coaxial cables.

Test cell 8 has a line 10 connected to it to carry a sample fluid entering cell 8. The sample fluid leaves test cell 8 by way of a line 11. Test cell 8 and the sample fluid will be described in more detail hereinafter. Suffice to say at this point that microwave energy from antenna 7 passes through the sample fluid and is received by an antenna 9. The microwave energy received by antenna 9 leaves test cell 8, and is provided as test microwave energy to a directional coupler 18. Directional coupler 18 provides the test microwave energy to a detector 22 and to a mixer 28. Detector 22 provides a signal E1 corresponding to the power of the microwave energy leaving test cell 8.

Phase shifter means 5 provides microwave energy, hereinafter called the reference microwave energy, to mixer 28 which mixes the reference microwave energy and the test microwave energy to provide two electrical signals E2, E3, representative of the phases of the reference microwave energy and the test microwave energy, respectively.

A differential amplifier 30 provides an output signal E0 in accordance with the difference between signals E2 and E3. Signal E0 is a function of the phase difference between the reference microwave energy and the test microwave energy and is provided to a feedback network 34. Feedback network 34 provides a signal C to phase shifter means 5, controlling the phase of the reference microwave energy, and to computer means 40. As a consequence of feedback circuit 34, signal E0 decreases in amplitude to zero at which time there is substantially 90° phase difference between the reference microwave energy and the test microwave energy. At this point phase shifter means 5 signals computer means 40 by the 'enable' signal causing computer means 40 to read signal C which was proportional to the phase difference between the test microwave energy and the reference microwave energy.

A temperature sensor 42 senses the temperature of test cell 8, and hence the temperature of the sample fluid in it, and provides a signal T corresponding to the sensed temperature.

Signals E1, T and C are provided to computer means 40 which contains within it memory means having data related to phase and power for various percentages of water cuts that could be encountered in the production stream. Phase Shifter 5 also provides an enable signal to computer means 40 allowing computer means 40 to utilize signals T, C and E1 to select the proper water cut value. Computer means 40 provides signals, corresponding to the selected water cut value, to readout means 44 which may be either display means or record means or a combination of the two.

The monitor of the present invention has various modes of operation. In this regard during the test mode of operation an inlet pipe 57 entered into a pipe 60 has a sample stream of a petroleum stream flowing in pipe 60 enter it. The test is to determine the water cut of the petroleum stream. The sample stream is provided to a three-way valve means 64. As the primary test mode is being discussed, the sample stream passes through three-way valve 64 into pipe 10. The sample stream flows through test cell 8, and pipe 11 and passes through another three-way valve means 68.

The sample stream leaves three-way valve means 68 by way of a pipe 71 and flows back into pipe 60. It should be noted that pipe 60 includes a choke 75 which is indicated by the dash line, which causes the petroleum stream to flow faster past outlet pipe 71, thus causing the liquid in line 60 to enter line 57 and exit line 71. Pipe 71 has a stub 77 with a valve 80 which may be used to vent any gases as needed.

In a second mode of operation, an inlet pipe 85 has a valve 87 and provides a sample of the petroleum stream to separation means 94. Valve 87 also may be used to effect an evacuation of fluids from separation means 94. Separation means 94 is connected to three-way valve means 64 by a pipe 97.

Three-way valve 68 is also connected to separation means 100 by a pipe 104. Separation means 100 is also connected to another pipe 108 having a valve 110. Pipe 108 is connected to an exit pipe 115 having a valve 116 which enters into pipe 60. A stub pipe 120 having a valve 125 is connected to pipes 108 and 115 and may be used to vent any gases occurring in those pipes.

Figure 2:
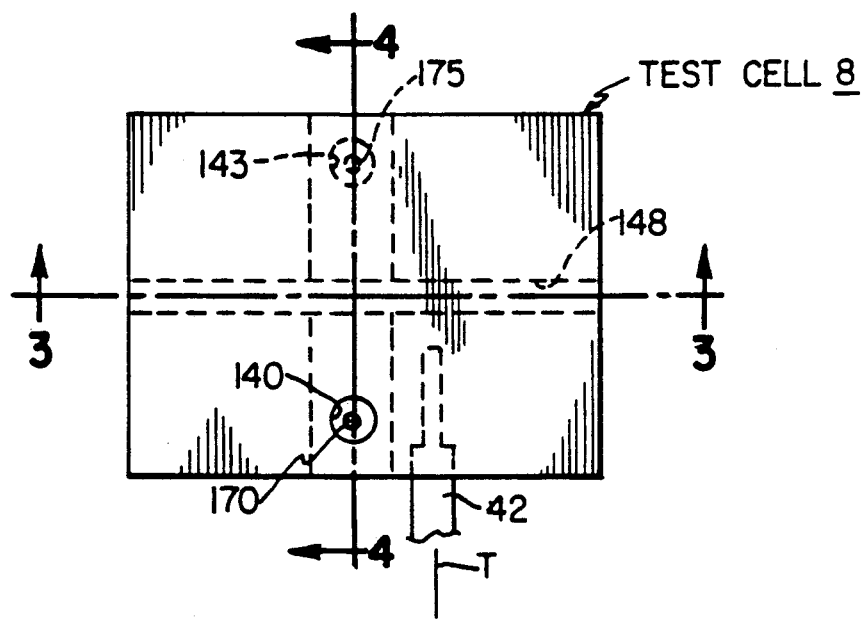
FIG. 2 is a drawing of the test cell shown in FIG. 1.

With reference to FIG. 2, there is shown test cell 8 having a microwave entrance port 140. On the other side of test cell 8 as represented by dash lines is a microwave exit port 143. Connecting microwave entrance port and microwave exit port is a microwave channel 158.

Figure 3:
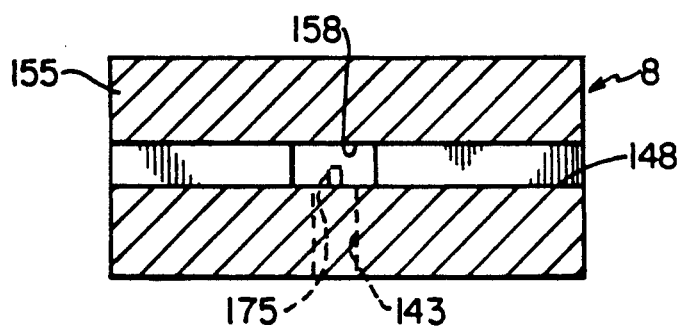
FIGS. 3 and 4 are cross-sectional drawings of the test cell shown in FIG. 2.

Also shown in FIG. 2 is a fluid channel 148. FIG. 3 has a cut away view of test cell 8 in the direction of the arrows 3—3. There is shown a body 155 which may be made of metal having fluid channel 148 passing through it along one axis and a microwave channel 158 for the microwave energy cut transversely through channel 148.

It should also be noted that fluid channel 148 have a rectangular cross-section so that the microwave energy that passes through the fluids, always has the same distance of passage.

Figure 4:
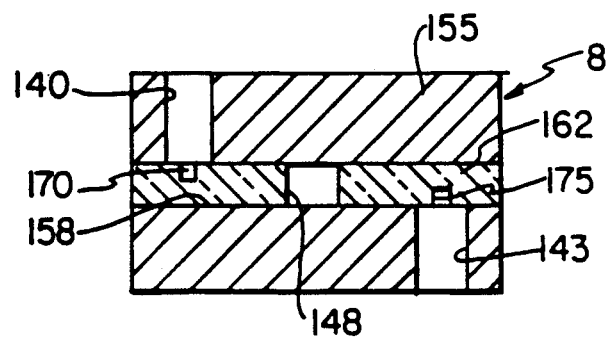

Referring to FIG. 4, there is a view of test cell 8 in the direction of 4—4, shown in FIG. 2. Channel 158 is filled with a solid material 162, such as high density Teflon, that is conductive to microwave energy, except for that portion of channel 158 that forms a cross-section of fluid channel 148. Cut into body 155 is microwave entrance port 140. Further there is another chamber 170 which connects microwave entrance port 190 and enters into material 162 in channel 158. This is for the insertion of microwave antenna 7, which may be of the commercial type made by Omni Spectra, Part No. 2057-5134. Similarly, microwave exit port 143, for antenna 9, is shown with an additional chamber 175 which enters into material 162. Basically it is the same type of antenna as is entered with entrance port 140, but again modified for the present application. The microwave energy when applied to the antenna 7 enters material 162 and is directed to cross channel 148 until it reaches the antenna 9 inserted in exit port 143.

Referring also to FIG. 1, lines 10 and 11 are connected in a conventional manner to channel 158 so that the sample fluid in line 10 will flow through test cell 53 if so desired.

As can be seen in FIG. 2, temperature sensor 46, which may be a thermocouple, is inserted into a chamber cut into body 155 and thus reads the temperature of body 155 as the temperature of the reference and as of the production stream sample.

The second mode of operation, is a calibration mode where the fluid sample in test cell 8 is tested under two static conditions rather than a flowing condition. The first static condition is achieved by permitting the sample fluid to flow through test cell 8 as previously described for the normal mode of testing and then operating three-way valves 64 and 68 simultaneously so that there is no longer any flow, thereby entrapping the fluid sample in test cell 8. After a predetermined time delay the fluid sample is tested as has been indicated by the normal operation. It should be noted that all valves, whether they are three-way valve means 64 and 68 or other valves shown are controlled by operation of computer means 40 although they can be controlled from an operator's console. A single dashed line, "valve control signals", indicates that each valve 80, 87, 110, 116 and 125 and each three way valve means 64 and 100 receives a separate control signal from computer means 40 and is controlled by that signal.

Use of one of two additional static modes of operation, namely a third mode and a fourth mode, generally completes calibration. In the third mode of operation, best suited for high oil content fluids, calibration parameters needed for the water phase may be determined after permitting the fluid sample to flow through lines 57 three-way valve means 64, lines 10 and 11, test cell 8, through three-way valve means 68 into separation means 100. At this point three-way valve means 64 is operated to prevent the fluid from returning back to the petroleum stream in pipe 60. Valve 110 is then operated so it will block further flow of the fluid. After a predetermined time delay the fluid sample is tested as has been indicated by the normal operation this measurement provides a calibration signal related to water properties.

In the fourth mode of operation, best suited for high water content fluids, oil measurements are made. Valve 87 is open to permit the fluid sample to flow into separation means 94 and thence through line 97 to three-way valve means 64. Three-way valve means 64 is controlled to permit the fluid to continue into lines 10 and 11 in test cell 8. After a short duration of flow from line 11 to line 71 or line 11 to line 109, three-way valve means 68 is operated so as not to permit passage of fluid into either line 104 or line 71. After lines 10 and 11 in test cell 8 are completely filled and hence separation means 94 of valve 87 is operated to close it so that it cannot leak back into the petroleum stream. Again after a predetermined time period, measurement is taken using the normal testing techniques mentioned. This measurement provides a calibration signal related to oil properties.

The fifth mode of operation is a flushing mode of operation, but it also fills both separation means. In this respect valves 87, 110 and 116 are activated to the open position so that fluid flows through line 85 into separation means 94 into line 97. Three-way valve means passes the fluid from line 97 to lines 10 into test cell 8 which in turn provides it to line 11. Three-way valve means 68 allows the fluid from line 11 to enter line 104 and into separation means 100. Separation means 100 then provides the sample fluid through valve 110 into line 108 in turn into line 115 and through valve 116 and finally back into pipe 60.

The fifth mode of operation provides an alternative means of filling separation means 100 and 94. During this operation closing either valve 64 momentarily reveals water data or closing valve 68 momentarily reveals oil data to the computer means. This alternative can be used in circumstances in which stopping oil flow completely is to be avoided due to corrosion or fouling problems.

In each case above computer means 40 collects phase and amplitude data and uses it to refer to the proper calibration constants in computer means 40 memory. These calibration constants are used to predict the correct water/oil ratio in the fluid normally passing through line 57 to line 10, to line 11 and to line 71.

What is claimed is:

1. A variable mode microwave water cut monitor for monitoring the water cut of a petroleum steam in a pipe, comprising:
   test cell means for containing a fluid sample of the petroleum stream;

fluid sample providing means connected to the test cell means for providing the fluid sample to the test cell means, in which the fluid sample providing means includes;

first ingress means arranged with the pipe carrying the petroleum stream for permitting the fluid sample to flow within the first ingress means, and first valve means connected to the control means and connecting the first ingress means to the test cell means for being responsive to a first control signal from the control means to control the flow of the fluid sample from the pipe to the test cell means.

said first valve means being a first three way valve having a first entrance port connected to the first ingress means, a second entrance port, and an exist port connected to the test cell means and responsive to the first command signal to pass a fluid present at its first entrance port to the exit port, to pass a fluid present at its second entrance port to the exit port or not to pass any fluid present at any entrance port; and further comprising second ingress means connected to the second entrance port of the first three way valve and to the pipe carrying the petroleum stream for receiving a fluid sample;

fluid sample exit means for allowing the fluid sample to exit the test cell means, which includes:

first egress means arranged with the pipe carrying the petroleum stream for allowing the fluid sample to flow through the first egress means into the pipe, and second valve means connected to the control means and connecting the first egress means to the test cell means for being responsive to a second control signal to control the flow of the fluid sample from the test cell means to the first egress means;

control means connected to the fluid sample providing means and to the fluid sample exiting means for controlling both of those means to effect different modes of operation for the monitor;

source means for transmitting microwave energy;

first antenna means connected to the source means for transmitting microwave energy into the fluid sample;

second antenna means for receiving microwave energy that has passed through the fluid sample fluid and providing the received microwave energy as test microwave energy;

detector means connected to the second antenna means for detecting the power of the test microwave energy and providing a power signal corresponding thereto; and indicator means connected to the second antenna means, to the source means and to the detector means for providing and indication of the water cut of the sample fluid in accordance with the power signal and the phase difference between the source provided microwave energy and the test microwave energy.

2. A monitor as described in claim 1 further comprising:

means for sensing the temperature of the sample fluid and providing a temperature signal corresponding thereto, and wherein the indicator means provides the indication of the water cut in accordance with the power signal, the temperature signal and the phase difference between the source provided energy and the received microwave energy.

3. A monitor as described in claim 2 in which the test cell means includes:

a body having a channel therein for the fluid sample and a channel therein for microwave energy passage, means for receiving the fluid sample and providing it to the fluid channel, means for allowing the fluid sample stream to exit from the body; and wherein the fluid channel and the microwave channel intersect each other at right angles.

4. A monitor as described in claim 3 in which the microwave channel contains a material, except for that portion of the microwave channel that crosses the fluid channel, that is impervious to fluids but permits passage of the microwave energy.

5. A monitor as described in claim 4 in which the first antenna means is spatially arranged with the microwave channel and transmits microwave energy into the microwave channel, and the second antenna means is spatially arranged with the microwave channel and receives microwave energy from the microwave channel.

6. A monitor as described in claim 5 in which the solid material in the microwave channel is Teflon.

7. A monitor as described in claim 6 in which the second ingress means including:

first pipe means arranged with the pipe carrying the petroleum stream for permitting the fluid sample to flow within the first pipe means, first separator means containing the fluid sample for allowing substantial separation of oil and water to occur, and third valve means connecting the first pipe means to the first separation means and connected to the control means for controlling the flow of the fluid sample into the first separation means in response to a third control signal.

8. A monitor as described in claim 7 in which the second valve means is a second three way valve having an entrance port connected to the test cell means, a first exit port connected to the first egress means and a second exit port and responsive to the second command signal to pass a fluid present at the entrance port to the first exit port, to pass a fluid present at the entrance port to the second exit port or not to pass a fluid present at the entrance port; and further comprising second egress means connected to the second exit port of the second three way valve and to the pipe carrying the petroleum stream for receiving the fluid sample from the second three way valve and for affecting the fluid sample.

9. A monitor as described in claim 8 in which the second egress means including:

second pipe means arranged with the pipe carrying the petroleum stream for permitting a fluid sample to flow within the pipe means, second separator means connected to the second pipe means for containing the fluid sample to allow separation of oil and water to occur, and third valve means connecting the second pipe means to the first separation means and connected to the control means for controlling the flow of a fluid sample from the second separation means into the pipe in accordance with a fourth control signal.

* * * * *